United States Patent
Garsuch et al.

(10) Patent No.: US 9,929,437 B2
(45) Date of Patent: Mar. 27, 2018

(54) USE OF REACTIVE IONIC LIQUIDS AS ADDITIVES FOR ELECTROLYTES IN SECONDARY LITHIUM ION BATTERIES

(71) Applicant: Gotion, Inc., Fremont, CA (US)

(72) Inventors: Arnd Garsuch, Ludwigshafen (DE); Karolin Geyer, Ludwigshafen (DE); Michael Schmidt, Alsbach-Haehnlein (DE); Martin Merger, Frankenthal (DE); Nicole Holub, Mannheim (DE)

(73) Assignee: Gotion Inc., Fremont, CA (US)

( * ) Notice: Subject to any disclaimer, the term of this patent is extended or adjusted under 35 U.S.C. 154(b) by 0 days.

(21) Appl. No.: 15/301,005

(22) PCT Filed: Mar. 31, 2015

(86) PCT No.: PCT/EP2015/057043
§ 371 (c)(1),
(2) Date: Sep. 30, 2016

(87) PCT Pub. No.: WO2015/150390
PCT Pub. Date: Oct. 8, 2015

(65) Prior Publication Data
US 2017/0033405 A1    Feb. 2, 2017

(30) Foreign Application Priority Data
Apr. 3, 2014    (EP) .................................... 14163429

(51) Int. Cl.
| | |
|---|---|
| *H01M 2/00* | (2006.01) |
| *H01M 10/0567* | (2010.01) |
| *C07C 309/20* | (2006.01) |
| *C07D 295/084* | (2006.01) |
| *H01G 11/06* | (2013.01) |
| *H01G 11/58* | (2013.01) |
| *H01G 11/64* | (2013.01) |
| *C07C 309/04* | (2006.01) |
| *C07D 295/088* | (2006.01) |
| *H01G 11/60* | (2013.01) |
| *H01M 10/0525* | (2010.01) |
| *H01M 10/0569* | (2010.01) |

(52) U.S. Cl.
CPC ....... *H01M 10/0567* (2013.01); *C07C 309/04* (2013.01); *C07C 309/20* (2013.01); *C07D 295/084* (2013.01); *C07D 295/088* (2013.01); *H01G 11/06* (2013.01); *H01G 11/58* (2013.01); *H01G 11/60* (2013.01); *H01G 11/64* (2013.01); *H01M 10/0525* (2013.01); *H01M 10/0569* (2013.01); *H01M 2300/0037* (2013.01); *Y02E 60/13* (2013.01)

(58) Field of Classification Search
CPC ........ H01G 11/64; H01G 11/06; H01G 11/58; C07C 309/20; C07D 295/084; Y02E 60/13
See application file for complete search history.

(56) References Cited

U.S. PATENT DOCUMENTS

| | | | | |
|---|---|---|---|---|
| 3,169,996 | A | * | 2/1965 | Bostian ................. C07C 37/685 159/DIG. 25 |
| 3,171,852 | A | * | 3/1965 | Distler ................... A01N 41/08 558/27 |

FOREIGN PATENT DOCUMENTS

WO    2013/026854    2/2013

OTHER PUBLICATIONS

[1-(Trimethylsiloxy)alkyl]triphenylphosphonium Salts: Syntheses and Utilization. Comparisons with Analogous Pyridinium Salts; Ernst Anders , Karola Hertlein, Achim Stankowiak, Erhard Irmer. Institut für Organische Chemie der Universität Erlangen-Nürnberg, Henkestraβe 42, D-8520 Erlangen, Germany 1992.*
STIC-EIC1700 Search, 2017.*
International Preliminary Report on Patentability dated Feb. 23, 2016, in Application No. PCT/EP2015/057043.
King J.F. et al., "Alkylation of Sulfonate Anions Via Substrate-Reagent Ion-Pair (SRIP) Reactions of [2]Betylates. Preparation of alkyl esters of hydroxyalkanesulfonic acids", Tetrahedron Letters, Pergamon, Department of Chemistry, University of Western Ontario, vol. 22, No. 37, Jan. 1, 1981, pp. 3573-3576 (XP002546398).
E. Anders et al., [1-(Trimethylsiloxy)alkyl]triphenylphosphonium salts: synthesis and utilization. Comparison with analogous pyridinium salts, Synthesis, vol. 23, Issue 41, Oct. 13, 1992, pp. 577-582 (XP002729484).
King J.F. et al., "Preparative Nucleophilic Substitution with "Betylates". Substrate Phase Transfer and Substrate-Reagent Ion-Pair Reactionst[1,2]", Journal of the American Chemical Society, vol. 100, 1978, pp. 1637-1639 (XP002729485).
King J.F. et al., "Betylates. 3. Preparative Nucleophilic Substitution by Way of [2]-, [3]-, and [4]Betylates. Stoichiometric Phase Transfer and Substrate-Reagent Ion-Pair (SRIP) Reactions of Betylates", Journal of the American Chemical Society, ACS Publications, US, vol. 104, Jan. 1, 1982, pp. 7108-7122 (XP002546399).

(Continued)

*Primary Examiner* — Mark F. Huff
*Assistant Examiner* — Monique M Wills
(74) *Attorney, Agent, or Firm* — Young Basile Hanlon & MacFarlane, P.C.

(57) ABSTRACT

The present invention relates to compounds of formula (I) wherein X is N or P; —$SO_3$— is —O—$S(O)_2$— or —$S(O)_2$—O—; and n and $R^1$ to $R^5$ are defined below, and to their use as additives for electrolyte compositions, in particular in electrolyte compositions for lithium batteries.

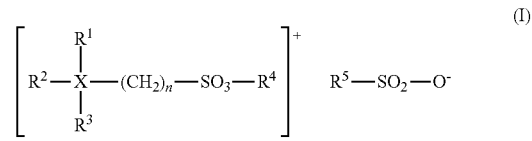

15 Claims, No Drawings

(56) References Cited

OTHER PUBLICATIONS

K. H. Yu et al., "Synthesis of [$^{18}$F]fluoroclofilium as a potential cardiac imaging agent for PET studies", Journal of Labelled Compounds and Radiopharmaceuticals, vol. 46, 2003, pp. 1151-1160 (XP002729508).

* cited by examiner

USE OF REACTIVE IONIC LIQUIDS AS ADDITIVES FOR ELECTROLYTES IN SECONDARY LITHIUM ION BATTERIES

The present invention relates to compounds of formula (I)

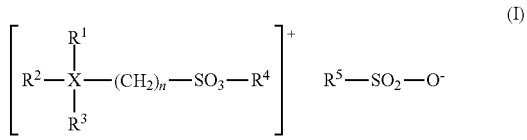

(I)

wherein X is N or P; —$SO_3$— is —O—$S(O)_2$— or —$S(O)_2$—O—; and n and $R^1$ to $R^5$ are defined below, and to their use as additives for electrolyte compositions, in particular in electrolyte compositions for lithium batteries.

Storing electrical energy is a subject of still growing interest. Efficient storage of electric energy would allow electric energy to be generated when it is advantageous and used when needed. Secondary electrochemical cells are well suited for this purpose due to their rechargeability. Secondary lithium batteries are of special interest for energy storage since they provide high energy density due to the small atomic weight and the large ionization energy of lithium and have become widely used as a power source for many portable electronics such as cellular phones, laptop computers, mini-cameras, etc.

In secondary lithium batteries like lithium ion batteries organic carbonates, ethers, esters and ionic liquids are used as sufficiently polar solvents. Most state of the art lithium ion batteries in general comprise not a single solvent but a solvent mixture of different organic aprotic solvents.

During charge and discharge of lithium ion batteries various reactions take place at different cell potentials. It is known that during the first charging process of a lithium ion battery usually a film is formed on the anode. This film is often called solid electrolyte interface (SEI). The SEI is permeable for lithium ions and protects the electrolyte from direct contact with the anode and vice versa. It is formed by reductive decomposition of components of the electrolyte composition like solvents, e.g. carbonates, esters, and ethers, and conductive salts on the surface of the anode, especially if the anode active material is a carbonaceous material like graphite. A certain amount of the lithium from the cathode is irreversibly consumed for the formation of the SEI and cannot be replaced. Structure and properties of the SEI may be significantly influenced by addition of suitable chemical compounds which are easily decomposed on the anode by reduction and thereby forming a film on the surface of the anode. This is also a possibility to reduce the amount of irreversibly consumed lithium. The SEI has a significant influence on cycling stability, calendar ageing, and durability (high-current resistance) of an electrochemical or electrooptical device. A well-known SEI forming additive is e.g. vinylene carbonate.

It is also known that certain ionic liquids containing reactive groups in the cation may be used as film forming additives for lithium batteries. Such reactive ionic liquids and their use as film forming additves in electrochemical cells are e.g. described in WO 2009/132740 A2. The ionic liquids according to WO 2009/132740 A2 are based on cations carrying an alkyl group interrupted by functional groups selected from carbonate, ester, and C—C double bond or wherein the alkyl group substituted by CN. The anions are selected from various voluminous anions like mixed fluoroalkyl/fluoro phosphates, fluoroalkylsulfonates and bis(fluoroalkylsulfone)imides.

WO 2013/026854 A1 describes ionic liquids suited as film forming additives wherein the cation contains an alkyl group containing a $SO_3$-group and wherein the alkyl group may additionally be interrupted by double bonds and ether bonds. As in the reactive ionic liquids of WO 2009/132740 A2 the anions are selected from various voluminous anions like mixed fluoroalkyl/fluoro phophates, fluoroalkylsulfonates and bis(fluoroalkylsulfone)imides.

The need for enhancing the lifetime of secondary batteries and a demand for electrolyte additives leading to a prolonged life time, cycle stability and high temperature stability of secondary electrochemical cells is still present. It was an object of the present invention to provide further additives for electrochemical applications leading to an improved lifetime, cycle stability and high temperature stability of electrochemical and electrooptical applications, in particular for secondary lithium cells like lithium batteries and lithium ion batteries.

This object is achieved by compounds of formula (I)

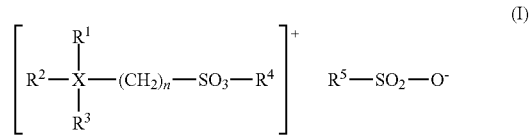

(I)

wherein
X is N or P;
—$SO_3$— is —O—$S(O)_2$— or —$S(O)_2$—O—;
$R^1$, $R^2$, and $R^3$ are selected independently from each other from $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the X-atom may be replaced by O, 1,2-epoxyethylene, cyclopropylene or $SO_3$;
or wherein $R^1$ and $R^2$ are linked and jointly selected from —$(CH_2)_m$— alkylene with m=4 or 5 forming together with the central X-atom a five- or six-membered heterocycle wherein one or more H of —$(CH_2)_m$— alkylene may be substituted by one or more substituents selected from F and optionally fluorinated $C_1$-$C_{10}$ alkyl, and wherein one or more $CH_2$ groups of —$(CH_2)_m$— alkylene may be replaced by O, S or NR';
R' is selected from $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene or $SO_3$;
n is an integer from 1 to 8 and wherein one or more $CH_2$ groups of the —$(CH_2)_n$— alkylene chain which are not directly bound to the X-atom or the $SO_3$ group may be replaced by O and wherein two adjacent $CH_2$ groups of the —$(CH_2)_n$— alkylene chain may be replaced by a C—C double bond or a C—C triple bond;
$R^4$ is selected from $C_1$-$C_6$ alkyl, $C_2$-$C_{20}$ alkenyl, $C_2$-$C_{20}$ alkynyl, $C_6$-$C_{12}$ aryl, and $C_7$-$C_{24}$ aralkyl, which may be substituted one or more groups selected from F, cyclopropyl, 1,2-epoxyethyl, and sulfonate, and wherein one or more CH$_2$ groups of alkyl, alkenyl, alkynyl and aralkyl which are not directly bound to the SO$_3$ group may be replaced by O, 1,2-epoxyethylene, cyclopropylene or SO$_3$;

R$^5$ is selected from C$_1$-C$_{20}$ alkyl, C$_2$-C$_{20}$ alkenyl, C$_2$-C$_{20}$ alkynyl, C$_6$-C$_{12}$ aryl, and C$_7$-C$_{24}$ aralkyl, wherein alkyl, alkenyl, alkynyl and aralkyl may be substituted by a group selected from cyclopropyl and 1,2-epoxyethyl, and wherein one or more CH$_2$ groups of alkyl, alkenyl, alkynyl and aralkyl which are not directly bound to the SO$_3$ group may be replaced by one or more groups selected from O, 1,2-epoxyethylene, cyclopropylene, SO$_3$, and NR"; and R" is selected from C$_1$-C$_{10}$ alkyl, C$_2$-C$_{10}$ alkenyl, C$_2$-C$_{10}$ alkynyl, C$_6$-C$_{12}$ aryl, and C$_7$-C$_{24}$ aralkyl, which be substituted by one or more groups selected from 1,2-epoxyethyl, cyclopropyl, and sulfonate, and wherein one or more CH$_2$ group of alkyl, alkenyl, alkynyl, and aralkyl, which are not directly bound to the N-atom may be replaced by O, 1,2-epoxyethylene, cyclopropylene or SO$_3$.

The problem is further solved by the use of at least one compound of formula (I) as additive in electrolyte compositions, by electrochemical compositions containing at least one compound of formula (I), and by electrochemical or electrooptical devices comprising at least one compound of formula (I).

The compounds of general formula (I) are also called reactive ionic liquids due to the presence of the SO$_3$-group in the cation. They show high reduction potentials indicating their suitability as film forming additives for electrochemical or electrooptical applications. The inventive compounds of formula (I) do not comprise anions like PF$_6^-$, which are susceptible to decomposition in the presence of water and thereby generating detrimental HF.

Secondary lithium ion batteries comprising an electrolyte composition containing a compound of formula (I) show good storability at elevated temperatures.

The term "C$_1$-C$_{20}$ alkyl" as used herein means a straight or branched saturated hydrocarbon group with 1 to 20 carbon atoms having one free valence and includes, e.g., methyl, ethyl, n-propyl, propyl, isopropyl, n-butyl, sec-butyl, isobutyl, tert-butyl, n-pentyl, iso-pentyl, 2,2-dimethylpropyl, n-hexyl, iso-hexyl, 2-ethyl hexyl, n-heptyl, iso-heptyl, n-octyl, iso-octyl, n-nonyl, n-decyl and the like. Preferred are C$_1$-C$_{10}$ alkyl groups, more preferred are C$_1$-C$_6$ alkyl groups, even more preferred are C$_1$-C$_4$ alkyl groups, and most preferred are methyl, ethyl, and 1- and 2-propyl.

The term "C$_2$-C$_{20}$ alkenyl" as used herein refers to an unsaturated straight or branched hydrocarbon group with 2 to 20 carbon atoms having one free valence. Unsaturated means that the alkenyl group contains at least one C=C double bond. C$_2$-C$_6$ alkenyl includes for example ethenyl, 1-propenyl, 2-propenyl, 1-n-butenyl, 2-n-butenyl, iso-butenyl, 1-pentenyl, 1-hexenyl, 1-heptenyl, 1-octenyl, 1-nonenyl, 1-decenyl and the like. Preferred are C$_2$-C$_{10}$ alkenyl groups, more preferred are C$_2$-C$_6$ alkenyl groups, even more preferred are C$_2$-C$_4$ alkenyl groups and in particular ethenyl and 1-propen-3-yl (allyl).

The term "C$_2$-C$_{20}$ alkynyl" as used herein refers to an unsaturated straight or branched hydrocarbon group with 2 to 20 carbon atoms having one free valence, wherein the hydrocarbon group contains at least one C—C triple bond. C$_2$-C$_6$ alkynyl includes for example ethynyl, 1-propynyl, 2-propynyl, 1-n-butinyl, 2-n-butynyl, iso-butinyl, 1-pentynyl, 1-hexynyl, -heptynyl, 1-octynyl, 1-nonynyl, 1-decynyl and the like and the like. Preferred are C$_2$-C$_{10}$ alkynyl, more preferred are C$_2$-C$_6$ alkynyl, even more preferred are C$_2$-C$_4$ alkynyl, in particular preferred are ethynyl and 1-propyn-3-yl (propargyl).

The term "C$_6$-C$_{12}$ aryl" as used herein denotes an aromatic 6- to 12-membered hydrocarbon cycle or condensed cycles having one free valence. Examples of C$_6$-C$_{12}$ aryl are phenyl and naphtyl. Preferred is phenyl.

The term "C$_7$-C$_{24}$ aralkyl" as used herein denotes an aromatic 6- to 12-membered aromatic hydrocarbon cycle or condensed aromatic cycles substituted by one or more C$_1$-C$_6$ alkyl. The C$_7$-C$_{24}$ aralkyl group contains in total 7 to 24 C-atoms and has one free valence. The free valence may be located at the aromatic cycle or at a C$_1$-C$_6$ alkyl group, i.e. C$_7$-C$_{24}$ aralkyl group may be bound via the aromatic part or via the alkyl part of the aralkyl group. Examples of C$_7$-C$_{24}$ aralkyl are methylphenyl, 1,2-dimethylphenyl, 1,3-dimethylphenyl, 1,4-dimethylphenyl, ethylphenyl, 2-propylphenyl, and the like.

The term "cyclopropylene" as used herein means the group derived from cyclopropane molecule having two free valences at two adjacent C-atoms:

the asterisks denote the two free valences.

The term "1,2-epoxyethyl" as used herein means an oxirane cycle having one free valence:

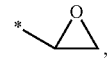

the asterisk denotes the free valence.

The term "1,2-epoxyethylene" as used herein means an oxirane cycle having two free valences at the two adjacent C-atoms:

the asterisks denote the free valences.

The term "contains at least one epoxy" as used herein means that at least one 1,2-epoxy group is contained. Both oxiranyl and oxirane-1,2-diyl contain the 1,2-epoxy group.

The term "sulfonate" as used herein means the groups —S(O)$_2$O—R''' wherein R''' is selected from C$_1$-C$_{10}$ alkyl, preferably from C$_1$-C$_6$ alkyl and more preferred from C$_1$-C$_4$ alkyl.

In the following the compounds of formula (I) are described in detail.

X is N or P, preferably X is N.

—SOs— is S(O)$_2$O— and —OS(O)$_2$—, preferably —SO$_3$— is —OS(O)$_2$—.

The cation of the compound of formula (I) contains a —(CH$_2$)$_n$— alkylene chain wherein n is an integer from 1 to 8, i.e. n is 1, 2, 3, 4, 5, 6, 7 or 8, preferably n is 1, 2, 3 or 4. One or more CH$_2$ groups of the —(CH$_2$)$_n$— alkylene chain which are not directly bound to the X-atom or the SO$_3$ group may be replaced by O and two adjacent CH$_2$ groups of the —(CH$_2$)$_n$— alkylene chain may be substituted by a C—C double bond or a C—C triple bond, i.e. a —($CH_2HCH_2$)— group may be substituted by a —(CH)═(CH)— group or a —(C)═(C)— group.

$R^1$ and $R^2$ are selected independently from each other from $C_1$-$C_{10}$ alkyl, $C_2$-$C_{10}$ alkenyl, $C_2$-$C_{10}$alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the X-atom may be replaced by O, 1,2-epoxyethylene, cyclopropylene or $SO_3$, preferably the X-atom may be replaced by O or $SO_3$; or $R^1$ and $R^2$ are linked and jointly selected from —($CH_2$)$_m$— alkylene with m=4 or 5 forming together with the central X-atom a five- or six-membered heterocycle wherein one or more H of —($CH_2$)$_m$— alkylene may be substituted by one or more substituents selected from F and optionally fluorinated $C_1$-$C_{10}$ alkyl, and wherein one or more $CH_2$ groups of —($CH_2$)$_m$— alkylene may be replaced by O, S or NR'.

If $R^1$ and $R^2$ are not linked, $R^1$ and $R^2$ are preferably selected independently from each other from $C_1$-$C_6$ alkyl, $C_2$-$C_6$ alkenyl, $C_2$-$C_6$ alkynyl, $C_6$-$C_{12}$ aryl, and $C_7$-$C_{18}$ aralkyl, and more preferred from $C_1$-$C_4$ alkyl, $C_2$-$C_4$ alkenyl, $C_2$-$C_4$ alkynyl, $C_6$-$C_{12}$ aryl, and $C_7$-$C_{14}$ aralkyl, and most preferred from $C_1$-$C_4$ alkyl, $C_2$-$C_4$ alkenyl, $C_2$-$C_4$ alkynyl, wherein alkyl, alkenyl, alkynyl, aryl and aralkyl may be substituted one or more groups selected from F, cyclopropyl, 1,2-epoxyethyl and sulfonate, and wherein one or more $CH_2$ group of alkyl, alkenyl, alkynyl and aralkyl which are not directly bound to the X-atom may be replaced by O or $SO_3$.

If $R^1$ and $R^2$ are linked they are preferably jointly selected from —($CH_2$)$_4$— alkylene forming together with the central X-atom a five-membered heterocycle wherein one or more H of —($CH_2$)$_4$— alkylene may be substituted by one or more substituents selected from F and optionally fluorinated $C_1$-$C_{10}$ alkyl, preferably from F and optionally fluorinated $C_1$-$C_4$ alkyl, and wherein one or more $CH_2$ groups of —($CH_2$)$_4$— alkylene may be replaced by O, S or NR'.

$R^1$ and $R^2$ are preferably linked and jointly selected from —($CH_2$)$_m$— alkylene with m=4 or 5 forming together with the central X-atom a five- or six-membered heterocycle, more preferred from —($CH_2$)$_4$— alkylene forming together with the central X-atom a five-membered heterocycle.

$R^3$ is selected independently from $R^1$ and $R^2$ from $C_1$-$C_{10}$ alkyl, $C_2$-$C_{10}$ alkenyl, $C_2$-$C_{10}$ alkynyl, $C_6$-$C_{12}$ aryl, and $C_6$-$C_{24}$ aralkyl, preferably from $C_1$-$C_6$ alkyl, $C_2$-$C_6$ alkenyl, $C_2$-$C_6$ alkynyl, $C_6$-$C_{12}$ aryl, and $C_7$-$C_{18}$ aralkyl, more preferred from $C_1$-$C_6$ alkyl, $C_2$-$C_6$ alkenyl, and $C_2$-$C_6$ alkynyl, wherein alkyl, alkenyl, alkynyl, aryl and aralkyl may substituted one or more groups selected from F, cyclopropyl, 1,2-epoxyethyl, and sulfonate, and wherein one or more $CH_2$ groups of alkyl, alkenyl, alkynyl and aralkyl which are not directly bound to the X-atom may be replaced by O, 1,2-epoxyethylene, cyclopropylene or $SO_3$, preferably by O or $SO_3$. $R^3$ preferably contains at least one reactive group selected from C—C double bond, C—C triple bond, cyclopropyl, cyclopropylene, and epoxy, more preferred $R^3$ contains at least one reactive group selected from C—C double bond, C—C triple bond, cyclopropyl, and epoxy.

R' is selected from $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, preferably from $C_1$-$C_6$ alkyl, $C_2$-$C_6$ alkenyl, $C_2$-$C_6$ alkynyl, $C_6$-$C_{12}$ aryl, and $C_7$-$C_{18}$ aralkyl, and more preferred from $C_1$-$C_4$ alkyl, $C_2$-$C_4$ alkenyl, $C_2$-$C_4$ alkynyl, $C_6$-$C_{12}$ aryl, and $C_7$-$C_{14}$ aralkyl, which may be substituted one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O. Most preferred R' is selected from $C_1$-$C_4$ alkyl and phenyl.

$R^4$ is selected from $C_1$-$C_{20}$ alkyl, $C_2$-$C_{20}$ alkenyl, $C_2$-$C_{20}$ alkynyl, $C_6$-$C_{12}$ aryl, and $C_7$-$C_{24}$ aralkyl, which may be substituted one or more groups selected from F, cyclopropyl, 1,2-epoxyethyl, and sulfonate, and wherein one or more $CH_2$ groups of alkyl, alkenyl, alkynyl and aralkyl which are not directly bound to the $SO_3$ group may be replaced by O, 1,2-epoxyethylene, cyclopropylene or $SO_3$, preferably by O or $SO_3$. Preferably $R^4$ is selected from $C_1$-$C_{10}$ alkyl, $C_2$-$C_{10}$ alkenyl, $C_2$-$C_{10}$ alkynyl, $C_6$-$C_{12}$ aryl, and $C_7$-$C_{18}$ aralkyl, more preferred from $C_1$-$C_6$ alkyl, $C_2$-$C_6$ alkenyl, $C_2$-$C_6$alkynyl, $C_6$-$C_{12}$ aryl, and $C_7$-$C_{14}$ aralkyl and most preferred from $C_1$-$C_6$ alkyl, $C_2$-$C_6$ alkenyl, and $C_2$-$C_6$ alkynyl, wherein alkyl, alkenyl, alkynyl, aryl and aralkyl may be substituted one or more groups selected from F, cyclopropyl, 1,2-epoxyethyl, and sulfonate, and wherein one or more $CH_2$ groups of alkyl, alkenyl, alkynyl and aralkyl which are not directly bound to the $SO_3$ group may be replaced by O. Preferably $R^4$ contains at least one reactive group selected from C—C double bond, C—C triple bond, cyclopropyl, cyclopropylene, and epoxy, more preferred $R^4$ contains at least one reactive group selected from C—C double bond, C—C triple bond, cyclopropyl, and epoxy.

In case $R^4$ is selected from alkyl it is in any case preferred that $R^4$ is selected from $C_1$-$C_6$ alkyl, i.e. in a preferred embodiment $R^4$ is selected from $C_1$-$C_6$ alkyl, $C_2$-$C_{20}$ alkenyl, $C_2$-$C_{20}$ alkynyl, $C_6$-$C_{12}$ aryl, and $C_7$-$C_{24}$ aralkyl, which may be substituted one or more groups selected from F, cyclopropyl, 1,2-epoxyethyl, and sulfonate, and wherein one or more $CH_2$ groups of alkyl, alkenyl, alkynyl and aralkyl which are not directly bound to the $SO_3$ group may be replaced by O, 1,2-epoxyethylene, cyclopropylene or $SO_3$, preferably by O or $SO_3$. Preferably $R^4$ is selected from $C_1$-$C_6$ alkyl, $C_2$-$C_{10}$ alkenyl, $C_2$-$C_{10}$ alkynyl, $C_6$-$C_{12}$ aryl, and $C_7$-$C_{18}$ aralkyl, more preferred from $C_1$-$C_6$ alkyl, $C_2$-$C_6$ alkenyl, $C_2$-$C_6$ alkynyl, $C_6$-$C_{12}$ aryl, and $C_7$-$C_{14}$ aralkyl and most preferred from $C_1$-$C_6$ alkyl, $C_2$-$C_6$ alkenyl, and $C_2$-$C_6$ alkynyl, wherein alkyl, alkenyl, alkynyl, aryl and aralkyl may be substituted one or more groups selected from F, cyclopropyl, 1,2-epoxyethyl, and sulfonate, and wherein one or more $CH_2$ groups of alkyl, alkenyl, alkynyl and aralkyl which are not directly bound to the $SO_3$ group may be replaced by O. Preferably $R^4$ contains at least one reactive group selected from C—C double bond, C—C triple bond, cyclopropyl, cyclopropylene, and epoxy, more preferred $R^4$ contains at least one reactive group selected from C—C double bond, C—C triple bond, cyclopropyl, and epoxy.

$R^5$ is selected from $C_1$-$C_{20}$ alkyl, $C_2$-$C_{20}$ alkenyl, $C_2$-$C_{20}$ alkynyl, $C_6$-$C_{12}$ aryl, and $C_7$-$C_{24}$ aralkyl, wherein alkyl, alkenyl, alkynyl and aralkyl may be substituted by a group selected from cyclopropyl and 1,2-epoxyethyl, and wherein one or more $CH_2$ groups of alkyl, alkenyl, alkynyl and aralkyl which are not directly bound to the $SO_3$ group may be replaced by one or more groups selected from O, NR", 1,2-epoxyethylene, cyclopropylene, and $SO_3$, preferably by O or $SO_3$. Preferably $R^5$ is selected from $C_1$-$C_{10}$ alkyl, $C_2$-$C_{10}$ alkenyl, $C_2$-$C_{10}$ alkynyl, $C_6$-$C_{12}$ aryl, and $C_7$-$C_{18}$ aralkyl, more preferred from $C_1$-$C_6$ alkyl, $C_2$-$C_6$ alkenyl, $C_2$-$C_6$ alkynyl, $C_6$-$C_{12}$ aryl, and $C_7$-$C_{14}$ aralkyl, and most preferred from $C_1$-$C_6$ alkyl, $C_2$-$C_6$ alkenyl, and $C_2$-$C_6$ alkynyl, wherein alkyl, alkenyl, alkynyl and aralkyl may be substituted a group selected from be substituted by a group selected from cyclopropyl and 1,2-epoxyethyl, and wherein one or more $CH_2$ groups of alkyl, alkenyl, alkynyl and aralkyl which are not directly bound to the $SO_3$ group may be replaced by one or more groups selected from 1,2-epoxyethylene, cyclopropylene, O, and $SO_3$, preferred selected from 1,2-epoxyethylene, O, and $SO_3$. If $R^5$ is selected from alkyl, it is preferably selected from $C_2$-$C_{20}$ alkyl, more preferred from $C_2$-$C_{10}$ alkyl and even more preferred from $C_2$-$C_6$ alkyl. Preferably $R^5$ contains at least one reactive group selected from C—C double bond, C—C triple bond, cyclopropyl, 1,2-cyclopropylene, and epoxy, more preferred $R^5$ contains at least one reactive group selected from C—C double bond, C—C triple bond, cyclopropyl, and epoxy.

R" is selected from $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from 1,2-epoxyethyl, cyclopropyl, and sulfonate, and wherein one or more $CH_2$ group of alkyl, alkenyl, alkynyl and aralkyl which are not directly bound to the N-atom may be replaced by O, 1,2-epoxyethylene, cyclopropylene or $SO_3$. Preferably R" is selected from $C_1$-$C_6$ alkyl, $C_2$-$C_6$ alkenyl, $C_2$-$C_6$ alkynyl, $C_6$-$C_{12}$ aryl, and $C_7$-$C_{18}$ aralkyl and more preferred from $C_1$-$C_4$ alkyl, $C_2$-$C_4$ alkenyl, $C_2$-$C_4$ alkynyl, $C_6$-$C_{12}$ aryl, and $C_7$-$C_{14}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene or $SO_3$. Most preferred R" is selected from $C_1$-$C_4$ alkyl and phenyl.

Preferred compounds of formula (I) include
compounds of formula (I) wherein X is N and —$SO_3$— is —O—$S(O)_2$—;
compounds of formula (I) wherein at least one of $R^3$, $R^4$, and $R^5$ contains at least one reactive group selected from C—C double bond, C—C triple bond, cyclopropyl, cyclopropylene, and epoxy;
compounds of formula (I) wherein at least one of $R^3$, $R^4$, and $R^5$ contains at least one reactive group selected from C—C double bond, C—C triple bond, cyclopropyl, cyclopropylene, and epoxy, and wherein X is N;
compounds of formula (I) wherein at least one of $R^3$, $R^4$, and $R^5$ contains at least one reactive group selected from C—C double bond, C—C triple bond, cyclopropyl, cyclopropylene, and epoxy, and wherein —$SO_3$— is —O—$S(O)_2$—;
compounds of formula (I) wherein at least one of $R^3$, $R^4$, and $R^5$ contains at least one reactive group selected from C—C double bond, C—C triple bond, cyclopropyl, cyclopropylene, and epoxy, and wherein X is N and —$SO_3$— is —O—$S(O)_2$—;
compounds of formula (I) wherein $R^3$ contains at least one reactive group selected from C—C double bond, C—C triple bond, cyclopropyl, cyclopropylene, and epoxy; within these compounds it is preferred if X is N or —$SO_3$— is —O—$S(O)_2$—, and more preferred if X is N and —$SO_3$— is —O—$S(O)_2$—;
compounds of formula (I) wherein $R^4$ contains at least one reactive group selected from C—C double bond, C—C triple bond, cyclopropyl, cyclopropylene, and epoxy; within these compounds it is preferred if X is N or —$SO_3$— is —O—$S(O)_2$—, and more preferred if X is N and —$SO_3$— is —O—$S(O)_2$—;
compounds of formula (I) wherein $R^5$ contains at least one reactive group selected from C—C double bond, C—C triple bond, cyclopropyl, cyclopropylene, and epoxy; within these compounds it is preferred if X is N or —$SO_3$— is —O—$S(O)_2$—, and more preferred if X is N and —$SO_3$— is —O—$S(O)_2$—;
compounds of formula (I) wherein $R^4$ and $R^5$ are equal;
compounds of formula (I) wherein $R^4$ and $R^5$ are equal and X is N;
compounds of formula (I) wherein $R^4$ and $R^5$ are equal and —$SO_3$— is —O—$S(O)_2$—; and
compounds of formula (I) wherein $R^4$ and $R^5$ are equal, X is N, and —$SO_3$— is —O—$S(O)_2$—.

Preferred are also compounds of formula (Ia), wherein

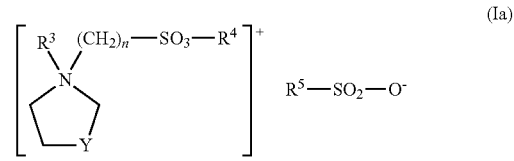

Y is selected from $CH_2$, O and NR', preferably Y is $CH_2$;
—$SO_3$— is —O—$S(O)_2$— or —$S(O)_2$—O—, preferably —$SO_3$— is —O—$S(O)_2$—; and
n, $R^3$, $R^4$, $R^5$, and R' are defined as described above or as described as being preferred.

Preferred compounds of formula (Ia) include compounds of formula (Ia) wherein $R^4$ and $R^5$ are equal, compounds of formula (Ia) wherein at least one of $R^3$, $R^4$, and $R^5$ contains at least one reactive group selected from double bond, C—C triple bond, cyclopropyl, cyclopropylene, and epoxy, and compounds of formula (Ia) wherein $R^4$ and $R^5$ are equal and at least one of $R^3$, $R^4$, and $R^5$ contains at least one reactive group selected from double bond, C—C triple bond, cyclopropyl, cyclopropylene, and epoxy.

Particular prefered compounds of formula (I) are

(IIa)

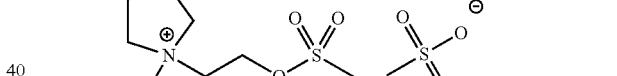

(IIb)

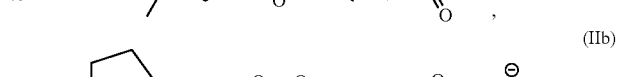

(IIc)

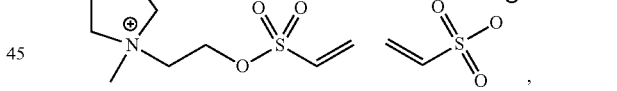

(IId)

(IIe)

-continued

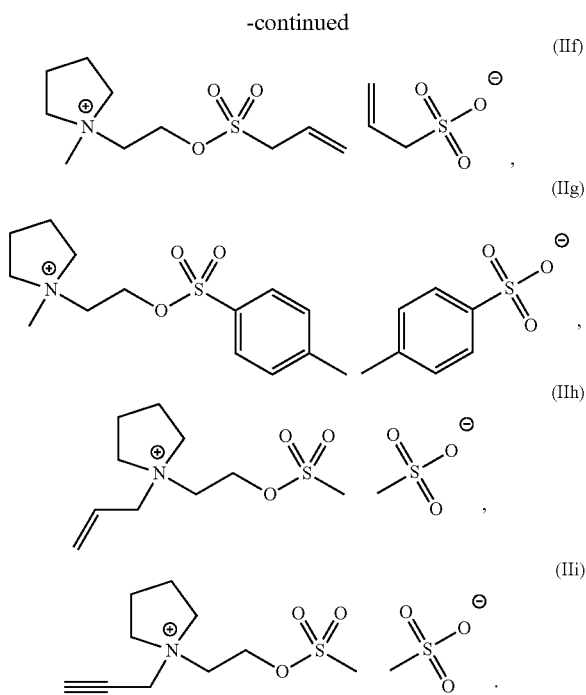

(IIf), (IIg), (IIh), (IIi)

The preparation of the compounds of formula (I) is in general known to the person skilled in the art. The cations may be prepared via the chlorides as described in WO 2013/026854 A1 but using salts of $R^5$—$SO_3^-$ anions like the lithium salts to transfer the chlorides into the inventive compounds containing $R^5$—$SO_3^-$ anions.

The present invention additionally provides a direct preparation process of compounds of formula (I) wherein —$SO_3$— is —O—$S(O)_2$—. These compounds may be prepared by reacting compounds of formula $XR^1R^2R^3$ with compounds of formula $R^4$—$S(O)_2$—O—$(CH_2)_n$—O—$S(O)_2$—$R^5$. The reaction may be performed by providing a mixture of diester $R^4$—$S(O)_2$—O—$(CH_2)_n$—O—$S(O)_2$—$R^5$ and an aprotic organic solvent like acetonitrile, acetone, ethyl methyl ketone, methyl isobutyl ketone, dichloromethane or toluene, and adding compound $XR^1R^2R^3$. $XR^1R^2R^3$ may be added in slight excess. The reaction may be carried out above room temperature, e.g. at 50 to 100° C. The reaction usually takes between 1 to 24 h. Subsequently the desired product is separated, optionally purified and dried. This direct preparation process of compounds of formula (I) wherein —$SO_3$— is —O—$S(O)_2$— is especially well suited for compounds of formula (I) wherein $R^4$ and $R^5$ are equal.

Viewed chemically, an electrolyte composition is any composition which comprises free ions and as a result is electrically conductive. The most typical electrolyte composition is an ionic solution, although molten electrolyte compositions and solid electrolyte compositions are likewise possible. An electrolyte composition of the invention is therefore an electrically conductive medium, primarily due to the presence of at least one substance which is present in a dissolved and/or molten state, i.e., an electrical conductivity supported by movement of ionic species.

The compounds of the formula (I), as described above or as described as being preferred, may be used as additive in an electrolyte composition. Therefore, a further object of the present invention is the use of compounds of formula (I) as described above as additives in electrolyte compositions, in particular their use as film forming additives in electrolyte compositions. The electrolyte compositions may be used in electrochemical or electrooptical devices, more particularly in lithium batteries, double layer capacitors, lithium ion capacitors, solar cells, electrochromic displays, sensors and/or biosensors.

For use in lithium batteries or lithium capacitors, the compounds of formula (I), as described above, are additives which are especially positive in their effect on the generation of the SEI, i.e. they are preferably used as film forming additives. Preferably the compounds of formula (I) are used as film forming additives in lithium batteries, in particular in lithium ion batteries For use in solar cells, electrochromatic devices, sensors or biosensors, the compounds of the formula I, as described above, take on the function of an additive.

Accordingly, when the compounds of the formula (I) are used as an additive in an electrolyte composition, the typical concentration is 0.001 to 10 wt.-%, preferred 0.01 to 2 wt.-% and most preferred 0.01 to 2.0 wt.-% based on the total weight of the electrolyte composition.

The invention additionally provides an electrolyte composition comprising at least one compound of formula (I), as described above or as described as being preferred. The typical concentration of the at least one compound of formula (I) is 0.001 to 10 wt.-%, preferred 0.01 to 2 wt.-% and most preferred 0.01 to 2.0 wt.-% based on the total weight of the electrolyte composition.

The inventive electrolyte composition is preferably liquid at working conditions; more preferred it is liquid at 1 bar and 25° C., even more preferred the electrolyte composition is liquid at 1 bar and −15° C., in particular the electrolyte composition is liquid at 1 bar and −30° C., even more preferred the electrolyte composition is liquid at 1 bar and −50° C.

The electrolyte composition contains at least one aprotic organic solvent, preferably at least two aprotic organic solvents. According to one embodiment the electrolyte composition may contain up to ten aprotic organic solvents.

The at least one aprotic organic solvent is preferably selected from (a) cyclic and acyclic organic carbonates, which may be partly halogenated, (b) di-$C_1$-$C_{10}$-alkylethers, which may be partly halogenated, (c) di-$C_1$-$C_4$-alkyl-$C_2$-$C_6$-alkylene ethers and polyethers, which may be partly halogenated, (d) cyclic ethers, which may be partly halogenated, (e) cyclic and acyclic acetales and ketales, which may be partly halogenated, (f) ortho esters, which may be partly halogenated, (g) cyclic and acyclic esters of carboxylic acids, which may be partly halogenated, (h) cyclic and acyclic sulfones, which may be partly halogenated, (i) cyclic and acyclic nitriles and dinitriles, which may be partly halogenated, and (j) ionic liquids.

If the electrolyte composition is intended for use in lithium ion batteries, the at least one aprotic organic solvent is preferably selected from solvents (a) to (i).

More preferred the at least one aprotic organic solvent is selected from cyclic and acyclic organic carbonates (a), di-$C_1$-$C_{10}$-alkylethers (b), di-$C_1$-$C_4$-alkyl-$C_2$-$C_6$-alkylene ethers and polyethers (c), cyclic und acyclic acetales and ketales (e) and cyclic and acyclic esters of carboxylic acids (g), even more preferred electrolyte composition contains at least one aprotic organic solvent selected from cyclic and acyclic organic carbonates (a) and most preferred electrolyte composition contains at least two aprotic organic solvents selected from cyclic and acyclic organic carbonates (a), in particular preferred electrolyte composition contains at least one aprotic solvent selected from cyclic organic carbonates and at least one aprotic organic solvent selected from acyclic organic carbonates.

The aprotic organic solvents (a) to (j) may be partly halogenated, e.g. they may be partly fluorinated, partly chlorinated or partly brominated, and preferably they may be partly fluorinated. "Partly halogenated" means, that one or more H of the respective molecule is substituted by a halogen atom, e.g. by F, Cl or Br. Preference is given to the substitution by F. The at least one solvent may be selected from partly halogenated and non-halogenated aprotic organic solvents (a) to (j), i.e. the electrolyte composition may contain a mixture of partly halogenated and non-halogenated aprotic organic solvents.

Examples of suitable organic carbonates (a) are cyclic organic carbonates according to the general formula (a1), (a2) or (a3)

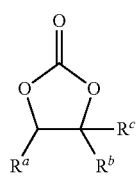 (a1)

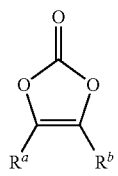 (a2)

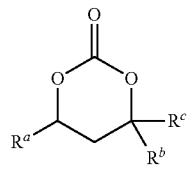 (a3)

wherein $R^a$, $R^b$ und $R^c$ being different or equal and being independently from each other selected from hydrogen; $C_1$-$C_4$-alkyl, preferably methyl; F; and $C_1$-$C_4$-alkyl substituted by one or more F, e.g. $CF_3$.

"$C_1$-$C_4$-alkyl" is intended to include methyl, ethyl, n-propyl, iso-propyl, n-butyl, iso-butyl, sec.-butyl and tert.-butyl.

Preferred cyclic organic carbonates (a) are of general formula (a1), (a2) or (a3) wherein $R^a$, $R^b$ and $R^c$ are H. Examples are ethylene carbonate, vinylene carbonate, and propylene carbonate. A preferred cyclic organic carbonate (a) is ethylene carbonate. Further preferred cyclic organic carbonates (a) are difluoroethylene carbonate (a4) and monofluoroethylene carbonate (a5)

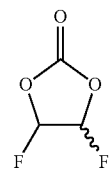 (a4)

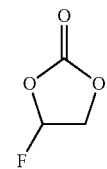 (a5)

Examples of suitable acyclic organic carbonates (a) are dimethyl carbonate, diethyl carbonate, methylethyl carbonate and mixtures thereof.

In one embodiment of the invention the electrolyte composition (A) contains mixtures of acyclic oganic carbonates (a) and cyclic organic carbonates (a) at a ratio by weight of from 1:10 to 10:1, preferred of from 3:1 to 1:1.

Examples of suitable acyclic di-$C_1$-$C_{10}$-alkylethers (b) are dimethylether, ethylmethylether, diethylether, diisopropylether, and di-n-butylether.

Examples of di-$C_1$-$C_4$-alkyl-$C_2$-$C_6$-alkylene ethers (c) are 1,2-dimethoxyethane, 1,2-diethoxyethane, diglyme (diethylene glycol dimethyl ether), triglyme (triethyleneglycol dimethyl ether), tetraglyme (tetraethyleneglycol dimethyl ether), and diethylenglycoldiethylether.

Examples of suitable polyethers (c) are polyalkylene glycols, preferably poly-$C_1$-$C_4$-alkylene glycols and especially polyethylene glycols. Polyethylene glycols may comprise up to 20 mol % of one or more $C_1$-$C_4$-alkylene glycols in copolymerized form. Polyalkylene glycols are preferably dimethyl— or diethyl— end-capped polyalkylene glycols. The molecular weight Mw of suitable polyalkylene glycols and especially of suitable polyethylene glycols may be at least 400 g/mol. The molecular weight Mw of suitable polyalkylene glycols and especially of suitable polyethylene glycols may be up to 5 000 000 g/mol, preferably up to 2 000 000 g/mol.

Examples of suitable cyclic ethers (d) are tetrahydrofurane and 1,4-dioxane.

Examples of suitable acyclic acetals (e) are 1,1-dimethoxymethane and 1,1-diethoxymethane. Examples for suitable cyclic acetals (e) are 1,3-dioxane and 1,3-dioxolane.

Examples of suitable ortho esters (f) are tri-$C_1$-$C_4$ alkoxy methane, in particular trimethoxymethane and triethoxymethane. Examples of suitable cyclic ortho esters (f) are 1,4-dimethyl-3,5,8-trioxabicyclo[2.2.2]octane and 4-ethyl-1-methyl-3,5,8-trioxabicyclo[2.2.2]octane.

Examples of suitable acyclic esters of carboxylic acids (g) are ethyl acetate, methyl butanoate, and esters of dicarboxylic acids like 1,3-dimethyl propanedioate. An example of a suitable cyclic ester of carboxylic acids (lactones) is γ-butyrolactone.

Examples of suitable cyclic and acyclic sulfones (h) are ethyl methyl sulfone, dimethyl sulfone, and tetrahydrothiophene-S,S-dioxide.

Examples of suitable cyclic and acyclic nitriles and dinitriles (i) are adipodinitrile, acetonitrile, propionitrile, and butyronitrile.

The water content of the inventive electrolyte composition is preferably below 100 ppm, based on the weight of the electrolyte composition, more preferred below 50 ppm, most preferred below 30 ppm. The water content may be determined by titration according to Karl Fischer, e.g. described in detail in DIN 51777 or ISO760:1978.

The content of HF of the inventive electrolyte composition is preferably below 60 ppm, based on the weight of the electrolyte composition, more preferred below 40 ppm, most preferred below 20 ppm. The HF content may be determined by titration according to potentiometric or potentiographic titration method.

The inventive electrolyte composition usually contains at least one conducting salt. The electrolyte composition functions as a medium that transfers ions participating in the electrochemical reaction taking place in an electrochemical cell. The conducting salt(s) present in the electrolyte are usually solvated in the aprotic organic solvent(s). Preferably the conducting salt is a lithium salt. The conducting salt is preferably selected from the group consisting of Li[$F_{6-x}P(C_yF_{2y}F_{2y+1})_x$], wherein x is an integer in the range from 0 to 6 and y is an integer in the range from 1 to 20;

Li[B(R$^I$)$_4$], Li[B(R$^I$)$_2$(OR$^{II}$O)] and Li[B(OR$^{II}$O)$_2$] wherein each R$^I$ is independently from each other selected from F, Cl, Br, I, $C_1$-$C_4$ alkyl, $C_2$-$C_4$ alkenyl, $C_2$-$C_4$ alkynyl, $OC_1$-$C_4$ alkyl, $OC_2$-$C_4$ alkenyl, and $OC_2$-$C_4$ alkynyl wherein alkyl, alkenyl, and alkynyl may be substituted by one or more OR$^{III}$, wherein R$^{III}$ is selected from $C_1$-$C_6$ alkyl, $C_2$-$C_6$ alkenyl, and $C_2$-$C_6$alkynyl, and (OR$^{II}$O) is a bivalent group derived from a 1,2- or 1,3-diol, a 1,2- or 1,3-dicarboxlic acid or a 1,2- or 1,3-hydroxycarboxylic acid, wherein the bivalent group forms a 5- or 6-membered cycle via the both oxygen atoms with the central B-atom;

LiClO$_4$; LiAsF$_6$; LiCF$_3$SO$_3$; Li$_2$SiF$_6$; LiSbF$_6$; LiAlCU, Li(N(SO$_2$F)$_2$), lithium tetrafluoro (oxalato) phosphate; lithium oxalate; and salts of the general formula Li[Z(C$_n$F$_{2n+1}$SO$_2$)$_m$], where m and n are defined as follows:

m=1 when Z is selected from oxygen and sulfur,
m=2 when Z is selected from nitrogen and phosphorus,
m=3 when Z is selected from carbon and silicon, and
n is an integer in the range from 1 to 20.

Suited 1,2- and 1,3-diols from which the bivalent group (OR$^{II}$O) is derived may be aliphatic or aromatic and may be selected, e.g., from 1,2-dihydroxybenzene, propane-1,2-diol, butane-1,2-diol, propane-1,3-diol, butan-1,3-diol, cyclohexyl-trans-1,2-diol and naphthalene-2,3-diol which are optionally are substituted by one or more F and/or by at least one straight or branched non fluorinated, partly fluorinated or fully fluorinated $C_1$-$C_4$ alkyl group. An example for such 1,2- or 1,3-diole is 1,1,2,2-tetra(trifluoromethyl)-1,2-ethane diol.

"Fully fluorinated $C_1$-$C_4$ alkyl group" means, that all H-atoms of the alkyl group are substituted by F.

Suited 1,2- or 1,3-dicarboxlic acids from which the bivalent group (OR$^{II}$O) is derived may be aliphatic or aromatic, for example oxalic acid, malonic acid (propane-1,3-dicarboxylic acid), phthalic acid or isophthalic acid, preferred is oxalic acid. The 1,2- or 1,3-dicarboxlic acid are optionally substituted by one or more F and/or by at least one straight or branched non fluorinated, partly fluorinated or fully fluorinated $C_1$-$C_4$ alkyl group.

Suited 1,2- or 1,3-hydroxycarboxylic acids from which the bivalent group (OR$^{II}$O) is derived may be aliphatic or aromatic, for example salicylic acid, tetrahydro salicylic acid, malic acid, and 2-hydroxy acetic acid, which are optionally substituted by one or more F and/or by at least one straight or branched non fluorinated, partly fluorinated or fully fluorinated $C_1$-$C_4$ alkyl group. An example for such 1,2- or 1,3-hydroxycarboxylic acids is 2,2-bis(trifluoromethyl)-2-hydroxy-acetic acid.

Examples of Li[B(R$^I$)$_4$], Li[B(R$^I$)$_2$(OR$^{II}$O)] and Li[B(OR$^I$O)$_2$] are LiBF$_4$, lithium difluoro oxalato borate and lithium dioxalato borate.

Preferably the at least one conducting salt is selected from LiPF$_6$, LiBF$_4$, and LiPF$_3$(CF$_2$CF$_3$)$_3$, more preferred the conducting salt is selected from LiPF$_6$ and LiBF$_4$, and the most preferred conducting salt is LiPF$_6$.

The at least one conducting salt is usually present at a minimum concentration of at least 0.01 wt.-%, preferably of at least 1 wt.-%, and more preferred of at least 5 wt.-%, based on the total weight of the electrolyte composition. Usually the upper concentration limit for the at least one conducting salt is 25 wt.-%, based on the total weight of the electrolyte composition.

The electrolyte composition may contain at least one further additive. The at least one further additive may be selected from usual additives for electrolyte composition like additional SEI forming additives, flame retardants, overcharge protection additives, HF and/or H$_2$O scavenger, stabilizer for LiPF$_6$ salt, wetting agents, ionic salvation enhancer, corrosion inhibitors, etc.

Examples of additional SEI forming additives are vinylene carbonate and its derivatives, fluorinated ethylene carbonates like monofluoro ethylene carbonate, the reactive ionic liquids described in WO 2009/132740 A2, the sulphur containing compounds described in WO 2013/026854, lithium oxalato borate, sultones like propane sultone and propene sultone, and the like.

Examples of flame retardants are organic phosphorous compounds like cyclophosphazenes, phosphoramides, alkyl and/or aryl tri-substituted phosphates, alkyl and/or aryl di- or tri-substituted phosphites, alkyl and/or aryl di-substituted phosphonates, alkyl and/or aryl tri-substituted phosphines, and fluorinated derivatives thereof.

Examples of overcharge protection additives are aromatic compounds like anisol derivatives, biphenyl and its derivatives, cyclohexylbenzene etc.

Examples of HF and/or H$_2$O scavenger are optionally halogenated cyclic and acyclic silylamines.

A compound added as further additive may have more than one effect in the electrolyte composition and the device comprising the electrolyte composition. E.g. lithium oxalato borate may be added as additive enhancing the SEI formation but may also be added as conducting salt.

If one or more further additives are present in the electrolyte composition, the total concentration of further additives is at least 0.001 wt.-%, preferred 0.005 to 5 wt.-% and most preferred 0.01 to 2 wt.-%, based on the total weight of the electrolyte composition.

When a solvent is present in the electrolyte of the invention there may also be a polymer included, the polymer being polyvinylidene fluoride, polyvinylidene-hexafluoropropylene copolymers, polyvinylidene-hexafluoropropylene-chlorotrifluoroethylene copolymers, Nafion, polyethylene oxide, polymethyl methacrylate, polyacrylonitrile, polypropylene, polystyrene, polybutadiene, polyethylene glycol, polyvinylpyrrolidone, polyaniline, polypyrrole and/or polythiophene. These polymers are added to the electrolytes in order to convert liquid electrolytes into quasi-solid or solid electrolytes and thus to improve solvent retention, especially during ageing.

The electrolyte compositions of the invention are prepared by methods which are known to the person skilled in the field of the production of electrolytes, generally by dissolving the conductive salt in the corresponding solvent mixture and adding the compounds of the formula (I) according to the invention, as described above.

The invention further provides an electrochemical or electrooptical device comprising at least one compound of the formula (I), as described above or as described as being preferred, and an electrochemical or electrooptical device comprising an electrolyte composition according to the invention.

The general construction of such electrochemical and electrooptical devices is known and is familiar to the person skilled in this art—for batteries, for example, in Linden's Handbook of Batteries (ISBN 978-0-07-162421-3).

The device may be a lithium battery, a double layer capacitor, a lithium ion capacitor, a solar cell, an electrochemical display, a sensor or a biosensor. The lithium battery is preferably a lithium ion battery; the solar cell is preferably a dye solar cell.

Preferably the electrochemical or electrooptical device is a lithium battery. The term "lithium battery" as used herein means an electrochemical cell, wherein the anode comprises lithium metal or lithium ions sometime during the charge/discharge of the cell. The anode may comprise lithium metal or a lithium metal alloy, a material occluding and releasing lithium ions, or other lithium containing compounds; e.g. the lithium battery may be a lithium ion battery, a lithium/sulphur battery, or a lithium/selenium sulphur battery.

In particular preferred the electrochemical device is a lithium ion battery, i.e. secondary lithium ion electrochemical cell comprising a cathode comprising a cathode active material that can reversibly occlude and release lithium ions and an anode comprising an anode active material that can reversibly occlude and release lithium ions. The terms "secondary lithium ion electrochemical cell" and "(secondary) lithium ion battery" are used interchangeably within the present invention.

The at least one cathode active material preferably comprises a material capable of occluding and releasing lithium ions selected from lithiated transition metal phosphates and lithium ion intercalating metal oxides.

Examples of lithiated transition metal phosphates are $LiFePO_4$ and $LiCoPO_4$, examples of lithium ion intercalating metal oxides are $LiCoO_2$, $LiNiO_2$, mixed transition metal oxides with layer structure having the general formula $Li(n-z)[Ni_aCO_bMn_c]_{(1-z)}O_{2+e}$ wherein z is 0 to 0.3; a, b and c may be same or different and are independently 0 to 0.8 wherein a+b+c=1; and $-0.1 \leq e \leq 0.1$, and manganese-containing spinels like LiMnCU and spinels of general formula $Li_{1+t}M_{2-t}O_{4-d}$ wherein d is 0 to 0.4, t is 0 to 0.4 and M is Mn and at least one further metal selected from the group consisting of Co and Ni, and $Li_{(1+g)}[Ni_hCO_iAl_j]_{(1-g)}O_{2+k}$. Typical values for g, h, l, j and k are: g=0, h=0.8 to 0.85, i=0.15 to 0.20, j=0.02 to 0.03 and k=0.

The cathode may further comprise electrically conductive materials like electrically conductive carbon and usual components like binders. Compounds suited as electrically conductive materials and binders are known to the person skilled in the art. For example, the cathode may comprise carbon in a conductive polymorph, for example selected from graphite, carbon black, carbon nanotubes, graphene or mixtures of at least two of the aforementioned substances. In addition, the cathode may comprise one or more binders, for example one or more organic polymers like polyethylene, polyacrylonitrile, polybutadiene, polypropylene, polystyrene, polyacrylates, polyvinyl alcohol, polyisoprene and copolymers of at least two comonomers selected from ethylene, propylene, styrene, (meth)acrylonitrile and 1,3-butadiene, especially styrene-butadiene copolymers, and halogenated (co)polymers like polyvinlyidene chloride, polyvinly chloride, polyvinyl fluoride, polyvinylidene fluoride (PVdF), polytetrafluoroethylene, copolymers of tetrafluoroethylene and hexafluoropropylene, copolymers of tetrafluoroethylene and vinylidene fluoride and polyacrylnitrile.

The anode comprised within the lithium batteries of the present invention comprises an anode active material that can reversibly occlude and release lithium ions or is capable to form an alloy with lithium. In particular carbonaceous material that can reversibly occlude and release lithium ions can be used as anode active material. Carbonaceous materials suited are crystalline carbon such as a graphite material, more particularly, natural graphite, graphitized cokes, graphitized MCMB, and graphitized MPCF; amorphous carbon such as coke, mesocarbon microbeads (MCMB) fired below 1500° C. and mesophase pitch-based carbon fiber (MPCF); hard carbon and carbonic anode active material (thermally decomposed carbon, coke, graphite) such as a carbon composite, combusted organic polymer, and carbon fiber.

Further anode active materials are lithium metal, or materials containing an element capable of forming an alloy with lithium. Non-limiting examples of materials containing an element capable of forming an alloy with lithium include a metal, a semimetal, or an alloy thereof. It should be understood that the term "alloy" as used herein refers to both alloys of two or more metals as well as alloys of one or more metals together with one or more semimetals. If an alloy has metallic properties as a whole, the alloy may contain a nonmetal element. In the texture of the alloy, a solid solution, a eutectic (eutectic mixture), an intermetallic compound or two or more thereof coexist. Examples of such metal or semimetal elements include, without being limited to, titanium (Ti), tin (Sn), lead (Pb), aluminum, indium (In), zinc (Zn), antimony (Sb), bismuth (Bi), gallium (Ga), germanium (Ge), arsenic (As), silver (Ag), hafnium (Hf), zirconium (Zr) yttrium (Y), and silicon (Si). Metal and semimetal elements of Group 4 or 14 in the long-form periodic table of the elements are preferable, and especially preferable are titanium, silicon and tin, in particular silicon. Examples of tin alloys include ones having, as a second constituent element other than tin, one or more elements selected from the group consisting of silicon, magnesium (Mg), nickel, copper, iron, cobalt, manganese, zinc, indium, silver, titanium (Ti), germanium, bismuth, antimony and chromium (Cr). Examples of silicon alloys include ones having, as a second constituent element other than silicon, one or more elements selected from the group consisting of tin, magnesium, nickel, copper, iron, cobalt, manganese, zinc, indium, silver, titanium, germanium, bismuth, antimony and chromium.

A further possible anode active material is silicon which is able to intercalate lithium ions. The silicon may be used in different forms, e.g. in the form of nanowires, nanotubes, nanoparticles, films, nanoporous silicon or silicon nanotubes. The silicon may be deposited on a current collector. The current collector may be a metal wire, a metal grid, a metal web, a metal sheet, a metal foil or a metal plate. Preferred the current collector is a metal foil, e.g. a copper foil. Thin films of silicon may be deposited on metal foils by any technique known to the person skilled in the art, e.g. by sputtering techniques. One possibility of preparing Si thin film electrodes are described in R. Elazari et al.; Electrochem. Comm. 2012, 14, 21-24. It is also possible to use a silicon/carbon composite as anode active material according to the present invention.

Other possible anode active materials are lithium ion intercalating oxides of Ti.

Preferably the anode active material is selected from carbonaceous material that can reversibly occlude and release lithium ions, particularly preferred the carbonaceous material that can reversibly occlude and release lithium ions is selected from crystalline carbon, hard carbon and amorphous carbon, in particular preferred is graphite. In another preferred embodiment the anode active is selected from silicon that can reversibly occlude and release lithium ions, preferably the anode comprises a thin film of silicon or a silicon/carbon composite. In a further preferred embodiment the anode active is selected from lithium ion intercalating oxides of Ti.

The anode and cathode may be made by preparing an electrode slurry composition by dispersing the electrode active material, a binder, optionally a conductive material and a thickener, if desired, in a solvent and coating the slurry composition onto a current collector. The current collector may be a metal wire, a metal grid, a metal web, a metal sheet, a metal foil or a metal plate. Preferred the current collector is a metal foil, e.g. a copper foil or aluminum foil.

The inventive lithium batteries may contain further constituents customary per se, for example separators, housings, cable connections etc. The housing may be of any shape, for example cuboidal or in the shape of a cylinder, the shape of a prism or the housing used is a metal-plastic composite film processed as a pouch. Suited separators are for example glass fiber separators and polymer-based separators like polyolefin separators.

Several inventive lithium batteries may be combined with one another, for example in series connection or in parallel connection. Series connection is preferred. The present invention further provides for the use of inventive lithium ion batteries as described above in devices, especially in mobile devices. Examples of mobile devices are vehicles, for example automobiles, bicycles, aircraft, or water vehicles such as boats or ships. Other examples of mobile devices are those which are portable, for example computers, especially laptops, telephones or electrical power tools, for example from the construction sector, especially drills, battery-driven screwdrivers or battery-driven tackers. But the inventive lithium ion batteries can also be used for stationary energy stores.

The invention further provides for the use of a compound of formula (I), as described above or as described as being preferred, in electrochemical or electrooptical devices, as described above.

Even without further statements, it is assumed that a skilled person is able to utilize the above description in its widest extent. Consequently, the preferred embodiments and examples are to be interpreted merely as a descriptive enclosure which in no way has any limiting effect at all.

The invention is illustrated by the examples which follow, which do not, however, restrict the invention.

1. Preparation of Compounds

Preparation of
2-(vinylsulfonyloxy)ethyl-methyl-pyrrolidinium vinylsulfonate (Compound 1)

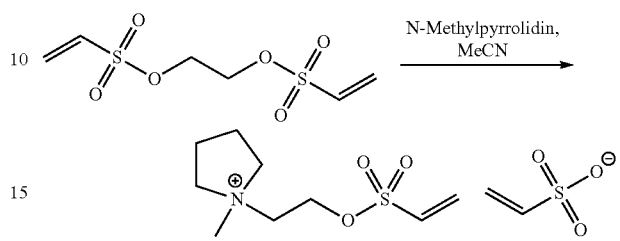

8 g of ethanediol-bis-vinylsulfonylester (1 eq.) and 200 ml acetonitrile were filled into a glass flask and were heated under stirring to about 70° C. 31 g methylpyrrolidine (1.1 eq.) were added within 60 min dropwise. The reaction mixture was stirred over night at 70° C. The reaction mixture was reduced to half of its volume by removing acetonitrile. Afterwards $CH_2Cl_2$ was added to yield a 1:1 mixture of $CH_2Cl_2$ and reaction mixture. This mixture was filtrated by means of silica gel. The silica gel was washed with $CH_2Cl_2$ and acetonitrile. The solvent was removed from the filtrate by evaporation with a rotary evaporator and the residue was dried overnight in oil pump vacuum. 70 g yellow viscous oil was obtained.

Preparation of
2-(methylsulfonyloxy)ethyl-methyl-pyrrolidinium methylsulfonate (Compound 2)

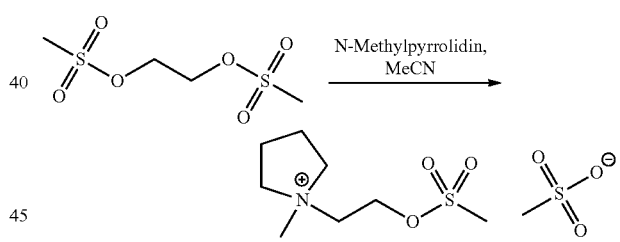

600 g ethandiol-bis-(methylsulfonyl)ester (1 eq.) and 1500 ml acetonitrile were filled into a reactor which was kept under nitrogen atmosphere. The mixture was heated under stirring to about 80° C. and 264 g methylpyrrolidin (1.1 eq.) was added at this temperature within 30 min. The reaction mixture was stirred over night at 80° C. Afterwards acetone was added dropwise and the reaction mixture was cooled down. Below 50° C. precipitation took place. The mixture was stirred for 3h at 5° C. and the precipitate was separated by suction. The filtration residue was washed with a 1:1 mixture of acrylonitrile and acetone, and 2 times with acetone and was dried in vacuum at room temperature. 675.5 g of slightly beige powder were obtained.

2. Electrochemical Tests

Corresponding electrolyte additives were further investigated in full cells at ambient temperature (25° C.). The coin type cell contains a stainless steel spacer to contact the graphite anode and a stainless steel casing bottom to contact the backside of the cathode. The cathode material NCM 111 ($LiNi_{0.33}Co_{0.33}Mn_{0.33}O_2$) was used to make cathode tapes with a capacity of 2 mAh/cm². Graphite-coated tapes (capacity about 2.2 mAh/cm²) were used as anodes. A glass-fiber filter separator (Whatmann GF/D) was used as the separator, which was soaked with 120 μl electrolyte. Coin type full cells were prepared with LiPF$_6$ (Kanto Denka Koyo Co. Ltd), which was dissolved in a 3:7 mixture of ethylene carbonate/ethyl methylcarbonate yielding a 1 M LiPF$_6$ solution. 0.5 wt.-% additive were added to the electrolyte mixture. All cells were assembled in an argon-filled glove box (Unilab, MBraun) having oxygen and water levels below 10 ppm. Afterwards the test cells were transferred to a battery test station. Electrochemical cycling (charging/discharging) was done using a Maccor battery test system. The full cells were initially held at open circuit potential for 2 hours and subsequently charged to 4.2 V. Afterwards the cells were discharged to a low voltage cutoff of 3.0 V. Prior the storage test all cells were cycled as follows: 1 cycle at 0.1 C, 1 cycle at 0.2 C, 10 cycles at 0.5 C at 25° C. (room temperature—RT). All cells (charged to 4.2 V) were disconnected and transferred to climate chamber operated at 60° C. after cycling at 25° C. The charged cells (4.2 V) were stored for 7 days at 60° C. The cell voltage and cell capacities before and after the 60° C. storage for 7 days are summarized in Table 1.

TABLE 1

| Additive | Cell voltage after 7 d storage at 60° C. | Discharge capacity after conditioning at RT | Discharge capacity after 7 d storage at 60° C. | Capacity retention after storage at 60° C. |
|---|---|---|---|---|
| Without (comparative) | 4.06 V | 134 mAh/g | 113 mAh/g | 84.0% |
| 2-(Vinylsulfonyloxy)ethyl-methyl-pyrrolidinium hexafluorophosphate (comparative) | 4.04 V | 132 mAh/g | 109 mAh/g | 82.6% |
| Compound 1 (inventive) | 4.06 V | 128 mAh/g | 116 mAh/g | 90.6% |

The addition of inventive compound (I) leads to an increase of the capacity retention after storage of the lithium ion battery at 60° C. in comparison to a non-inventive additive containing the same cation but a PF$_6$ anion.

The invention claimed is:

1. A compound of formula (I)

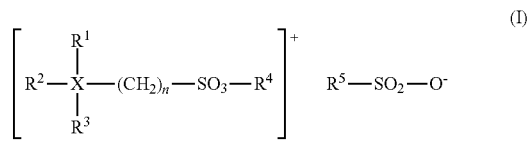

wherein

X is N or P;

—SO$_3$— is —O—S(O)$_2$— or —S(O)$_2$—O—;

R$^3$ is C$_1$-C$_{10}$ alkyl, C$_2$-C$_{10}$ alkenyl, C$_2$-C$_{10}$ alkynyl, C$_6$-C$_{12}$ aryl, and C$_7$-C$_{24}$ aralkyl, which may be substituted by one or more groups selected from F, cyclopropyl, 1,2-epoxyethyl, and sulfonate, and wherein one or more CH$_2$ groups of alkyl, alkenyl, alkynyl and aralkyl which are not directly bound to the X-atom may be replaced by O, 1,2-epoxyethylene, cyclopropylene or SO$_3$;

R$^1$ and R$^2$ are linked and jointly selected from —(CH$_2$)$_m$— alkylene with m=4 or 5 forming together with the central X-atom a five- or six-membered heterocycle wherein one or more H of —(CH$_2$)$_m$— alkylene may be substituted by one or more substituents selected from F and optionally fluorinated C$_1$-C$_{10}$ alkyl, and wherein one or more CH$_2$ groups of —(CH$_2$)$_m$— alkylene may be replaced by O, S or NR';

R' is selected from C$_1$-C$_{10}$ alkyl, C$_2$-C$_{10}$ alkenyl, C$_2$-C$_{10}$ alkynyl, C$_6$-C$_{12}$ aryl, and C$_7$-C$_{24}$ aralkyl, which may be substituted one or more groups selected from F, cyclopropyl, 1,2-epoxyethyl, and sulfonate, and wherein one or more CH$_2$ groups of alkyl, alkenyl, alkynyl and aralkyl which are not directly bound to the N-atom may be replaced by O, 1,2-epoxyethylene, cyclopropylene or SO$_3$;

n is an integer from 1 to 8 and wherein one or more CH$_2$ groups of the —(CH$_2$)$_n$-alkylene chain which are not directly bound to the X-atom or the SO$_3$ group may be replaced by O and wherein two adjacent CH$_2$ groups of the —(CH$_2$)$_n$— alkylene chain may be replaced by a C—C double bond or a C—C triple bond;

R$^4$ is selected from C$_1$-C$_6$ alkyl, C$_2$-C$_{20}$ alkenyl, C$_2$-C$_{20}$ alkynyl, C$_6$-C$_{12}$ aryl, and C$_7$-C$_{24}$ aralkyl, which may be substituted one or more groups selected from F, cyclopropyl, 1,2-epoxyethyl, and sulfonate, and wherein one or more CH$_2$ groups of alkyl, alkenyl, alkynyl and aralkyl which are not directly bound to the SO$_3$ group may be replaced by O, 1,2-epoxyethylene, cyclopropylene or SO$_3$;

R$^5$ is selected from C$_1$-C$_{20}$ alkyl, C$_2$-C$_{20}$ alkenyl, C$_2$-C$_{20}$ alkynyl, C$_6$-C$_{12}$ aryl, and C$_7$-C$_{24}$ aralkyl, wherein alkyl, alkenyl, alkynyl and aralkyl may be substituted by a group selected from cyclopropyl and 1,2-epoxyethyl, and wherein one or more CH$_2$ groups of alkyl, alkenyl, alkynyl and aralkyl which are not directly bound to the SO$_3$ group may be replaced by one or more groups selected from O, 1,2-epoxyethylene, cyclopropylene, SO$_3$, and NR''; and R'' is selected from C$_1$-C$_{10}$ alkyl, C$_2$-C$_{10}$ alkenyl, C$_2$-C$_{10}$ alkynyl, C$_6$-C$_{12}$ aryl, and C$_7$-C$_{24}$ aralkyl, which be substituted by one or more groups selected from 1,2-epoxyethyl, cyclopropyl, and sulfonate, and wherein one or more CH$_2$ group of alkyl, alkenyl, alkynyl, and aralkyl, which are not directly bound to the N-atom may be replaced by O, 1,2-epoxyethylene, cyclopropylene or SO$_3$.

2. The compounds compound according to claim 1, wherein X is N.

3. The compound according to claim 1, wherein —SO$_3$— is —O—S(O)$_2$—.

4. The compound according to claim 1, wherein n is 1, 2, 3 or 4.

5. The compound according to claim 1, wherein R$^4$ and R$^5$ are equal.

6. The compound according to claim 1, wherein R$^4$ comprises at least one reactive group selected from the group consisting of C=C double bond, C=C triple bond, cyclopropyl, cyclopropylene, and epoxy.

7. The compound according to claim 1, wherein $R^5$ comprises at least one reactive group selected from the group consisting of C=C double bond, C=C triple bond, cyclopropyl, cyclopropylene, and epoxy.

8. The compound according to claim 1, wherein $R^5$ comprises at least one reactive group selected from the group consisting of C=C double bond, C=C triple bond, cyclopropyl, cyclopropylene, and epoxy.

9. The compound according to claim 1, wherein $-SO_3-$ is $-O-S(O)_2$ and is obtained by reacting a compound of formula $XR^1R^2R^3$ with a compound of formula $R^4-S(O)_2O-(CH_2)_n-O-S(O)_2R^5$.

10. An electrolyte composition containing comprising at least one compound of formula (I) according to claim 1.

11. An electrolyte composition according to claim 10, which further comprises at least one organic aprotic solvent selected from the group consisting of:
   (a) cyclic and acyclic organic carbonates, which may be partly halogenated,
   (b) di-$C_1$-$C_{10}$-alkylethers, which may be partly halogenated,
   (c) di-$C_1$-$C_4$-alkyl-$C_2$-$C_6$-alkylene ethers and polyethers, which may be partly halogenated,
   (d) cyclic ethers, which may be partly halogenated,
   (e) cyclic and acyclic acetales and ketales, which may be partly halogenated,
   (f) orthocarboxylic acids esters, which may be partly halogenated,
   (g) cyclic and acyclic esters of carboxylic acids, which may be partly halogenated,
   (h) cyclic and acyclic sulfones, which may be partly halogenated, and
   (i) cyclic and acyclic nitrites and dinitriles, which may be partly halogenated.

12. An electrochemical or electrooptical device, comprising at least one compound of formula (I) according to claim 1.

13. The electrochemical or electrooptical device according to claim 12, wherein the electrochemical or electrooptical device is a lithium battery.

14. A method of making an electrolyte composition, the method comprising: adding at least one compound according to claim 1 to a composition that comprises a solvent and a conductive salt.

15. A method of forming a film on an anode, the method comprising: reducing at least one compound according to claim 1 on a surface of an anode, said anode being present in a lithium ion battery.

* * * * *